(12) United States Patent
Rys et al.

(10) Patent No.: US 9,579,500 B2
(45) Date of Patent: Feb. 28, 2017

(54) TINE FIXATION COMPONENTS FOR IMPLANTABLE MEDICAL DEVICES

(71) Applicant: Medtronic, Inc., Minneapolis, MA (US)

(72) Inventors: Kenneth D Rys, Minneapolis, MN (US); Thomas A Anderson, New Hope, MN (US); Vladimir Grubac, Brooklyn Park, MN (US); Jonathan L Kuhn, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/831,417

(22) Filed: Aug. 20, 2015

(65) Prior Publication Data

US 2015/0352353 A1    Dec. 10, 2015

Related U.S. Application Data

(62) Division of application No. 13/955,127, filed on Jul. 31, 2013, now Pat. No. 9,119,959.

(51) Int. Cl.
*A61N 1/05* (2006.01)
*A61N 1/375* (2006.01)
*A61N 1/372* (2006.01)
*A61N 1/362* (2006.01)

(52) U.S. Cl.
CPC ............ *A61N 1/0573* (2013.01); *A61N 1/362* (2013.01); *A61N 1/3756* (2013.01); *A61N 1/37205* (2013.01); *A61N 2001/0585* (2013.01)

(58) Field of Classification Search
CPC ....... A61N 1/057; A61N 1/1573; A61N 1/059
USPC ........................................ 607/126, 128, 130
See application file for complete search history.

(56) References Cited

U.S. PATENT DOCUMENTS

| | | |
|---|---|---|
| 3,814,104 A | 6/1974 | Irnich et al. |
| 4,103,690 A | 8/1978 | Harris |
| 5,492,119 A | 2/1996 | Abrams |
| 6,684,109 B1 | 1/2004 | Osypka |
| 7,149,587 B2 | 12/2006 | Wardle et al. |

(Continued)

FOREIGN PATENT DOCUMENTS

| | | |
|---|---|---|
| EP | 0 212 955 A2 | 3/1987 |
| WO | 95/20993 | 8/1995 |

(Continued)

OTHER PUBLICATIONS (PCT/US2014/048264) PCT Notification of Transmittal of the International Search Report and the Written Opinion of the International Searching Authority.

(Continued)

*Primary Examiner* — Paula J Stice (57) ABSTRACT

A tine portion for an implantable medical device includes a hook segment and a distal segment terminated by a tissue-piercing tip, wherein the distal segment extends from the hook segment to the tip. The hook segment, which is elastically deformable from a pre-set curvature, has one of: a round cross-section and an elliptical cross-section, while the distal segment has a flattened, or approximately rectangular cross-section. One or a pair of the tine portions may be integrally formed, with a base portion, from a superelastic wire, wherein the base portion is configured to fixedly attach to the device, for example, being captured between insulative members of a fixation subassembly.

18 Claims, 10 Drawing Sheets

(56) References Cited

U.S. PATENT DOCUMENTS

| | | |
|---|---|---|
| 7,509,169 B2 | 3/2009 | Eigler et al. |
| 8,452,420 B2 | 5/2013 | Flach et al. |
| 2006/0247753 A1 | 11/2006 | Wenger et al. |
| 2011/0251660 A1 | 10/2011 | Griswold |
| 2011/0251662 A1 | 10/2011 | Griswold et al. |
| 2012/0108986 A1 | 5/2012 | Beasley et al. |
| 2012/0116489 A1 | 5/2012 | Khairkhahan et al. |
| 2012/0172690 A1 | 7/2012 | Anderson et al. |
| 2012/0172892 A1 | 7/2012 | Grubac et al. |
| 2012/0232565 A1 | 9/2012 | Kveen et al. |

FOREIGN PATENT DOCUMENTS

| | | |
|---|---|---|
| WO | 01/02053 A1 | 1/2001 |
| WO | 2012135530 A1 | 4/2012 |

OTHER PUBLICATIONS (PCT/US2014/048213) PCT Notification of Transmittal of the International Search Report and the Written Opinion of the International Searching Authority.
(PCT/US2014/047962) PCT Notification of Transmittal of the International Search Report and the Written Opinion of the International Searching Authority, Mailed Oct. 10, 2014, 11 pages.
Chinese Office Action, Application No. 201480036180.7, mailed Nov. 16, 2016, Chinese language, 6 pages.
Chinese Office Action, Application No. 201480036180.7, mailed Nov. 16, 2016, English language translation, 5 pages.

TINE FIXATION COMPONENTS FOR IMPLANTABLE MEDICAL DEVICES

RELATED APPLICATION

This application is a divisional of U.S. patent application Ser. No. 13/955,127, filed Jul. 31, 2013 and issued as U.S. Pat. No. 9,119,959 which is entitled "TINE FIXATION COMPONENTS FOR IMPLANTABLE MEDICAL DEVICES", herein incorporated by reference in its entirety.

CROSS-REFERENCE TO RELATED APPLICATION

The present application is related to the commonly-assigned U.S. patent application Ser. No. 13/955,393, filed Jul. 31, 2013 and U.S. patent application Ser. No. 13/955,674, filed Jul. 31, 2013 and issued as U.S. Pat. No. 9,155,882 both of which are incorporated herein by reference, in their entirety.

TECHNICAL FIELD

The present invention pertains to implantable medical devices, and, more specifically, to tissue-penetrating fixation components and subassemblies thereof.

BACKGROUND

Figure 1:
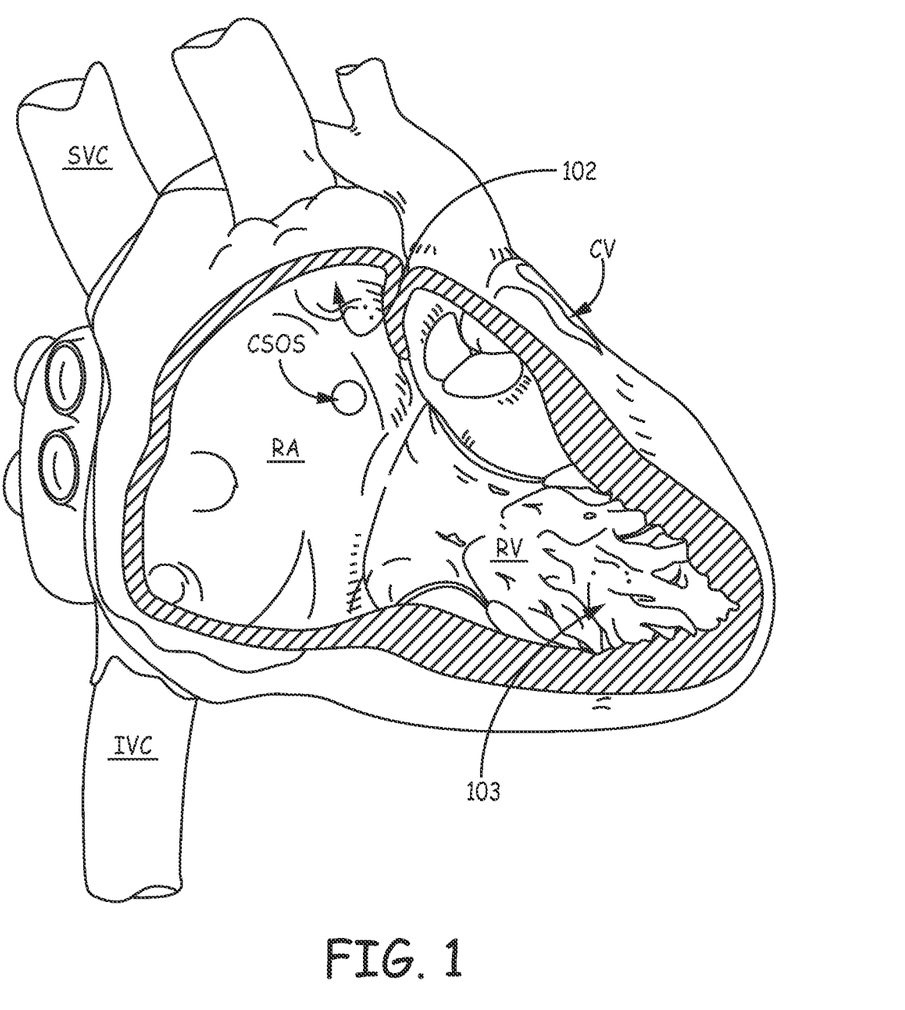
FIG. 1 is a schematic diagram showing potential implant sites for embodiments of the present invention.
Figure 2:
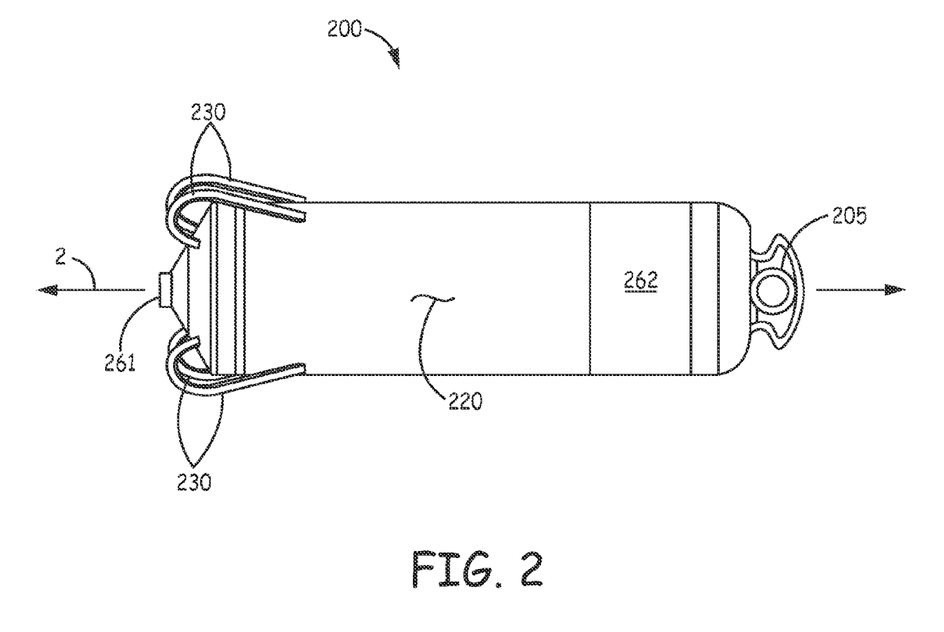
FIG. 2 is a plan view of an exemplary implantable medical device.

An implantable medical device, for the delivery of stimulation therapy and/or for diagnostic sensing, may include at least one tissue-penetrating fixation component configured to hold the device at an implant location. FIG. 1 is a schematic diagram that shows potential cardiac implant sites for such a device, for example, within an appendage 102 of a right atrium RA, within a coronary vein CV (via a coronary sinus ostium CSOS), or in proximity to an apex 103 of a right ventricle RV. FIG. 2 is a plan view of an exemplary implantable medical device 200, which includes a tissue-penetrating fixation component formed by a plurality of tine portions 230. FIG. 2 further illustrates device 200 including a hermitically sealed housing 220 that contains control electronics and a power source (not shown), and which defines a longitudinal axis 2 of device 200. Housing 220 may be formed from a medical grade stainless steel or titanium alloy and have an insulative layer formed thereover, for example, parylene, polyimide, or urethane. With further reference to FIG. 2, device 200 includes a pair of electrodes 261, 262, which may form a bipolar pair for cardiac pacing and sensing; tine portions 230 surround electrode 261 and are configured to penetrate tissue in order to hold electrode 261 in intimate contact with tissue, for example, at one of the aforementioned implant sites, while securing, or fixating device 200 for chronic implantation at the site. Further description of a suitable construction for device 200 may be found in the co-pending and commonly assigned United States Patent Application having the pre-grant publication number 2012/0172690 A1.

Figure 3A:
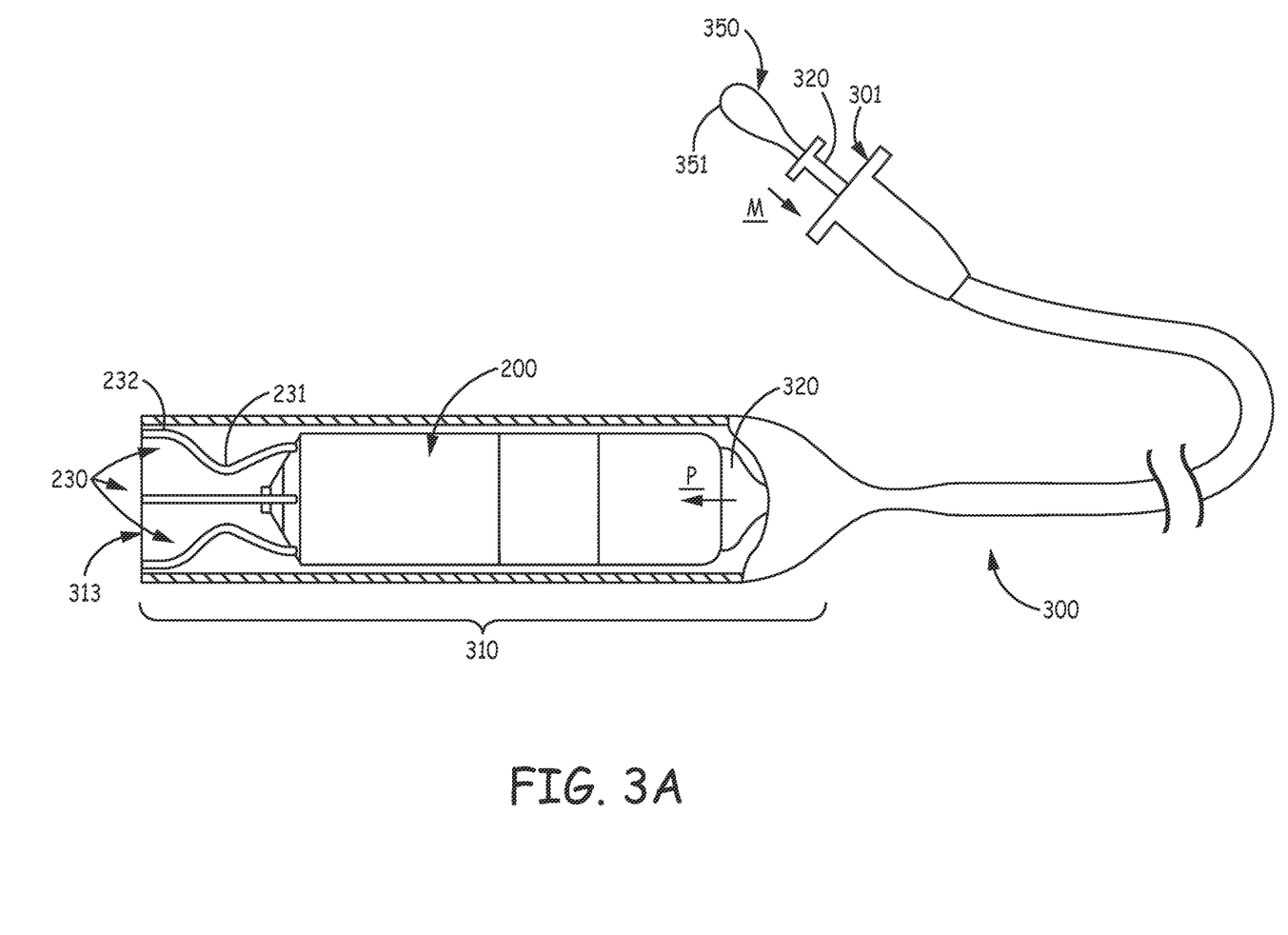
FIG. 3A is a plan view of the medical device loaded in a delivery catheter, according to some embodiments, wherein tine portions of a tissue-penetrating fixation component thereof are elastically deformed into an open position.

With reference to FIG. 3A, device 200 may be delivered to an implant location via a delivery catheter 300. For example, with reference to FIG. 1, if the target implant site is located in the right atrium RA, coronary vein CV, or right ventricle RV, a distal end 310 of catheter 300 may be maneuvered into the heart through a superior vena cava SVC or an inferior vena cava IVC, according to a transvenous delivery method known in the art. FIG. 3A shows a partial cross-section of distal end 310 of catheter 300, which is formed like a cup to hold and contain device 200 for delivery to the implant site. FIG. 3A illustrates device 200 having been loaded into distal end 310 so that a hook segment 231 of each tine portion 230 is elastically deformed, from a pre-set curvature thereof, to an open position, at which a distal segment 232 of each tine portion 230 extends distally toward an opening 313 of catheter distal end 310. Each tine portion 230 is preferably formed from a superelastic material, such as Nitinol. FIG. 3A further illustrates a deployment element 320 abutting a proximal end of device 200 and extending proximally therefrom, through a lumen of catheter 300, and out from a proximal opening 301 thereof. Element 320 may be moved, per arrow M, by an operator to push device 200, per arrow P, out from opening 313 of distal end 310, for example, when opening 313 has been located by the operator in close proximity to tissue at the target implant site.

Figure 3B:
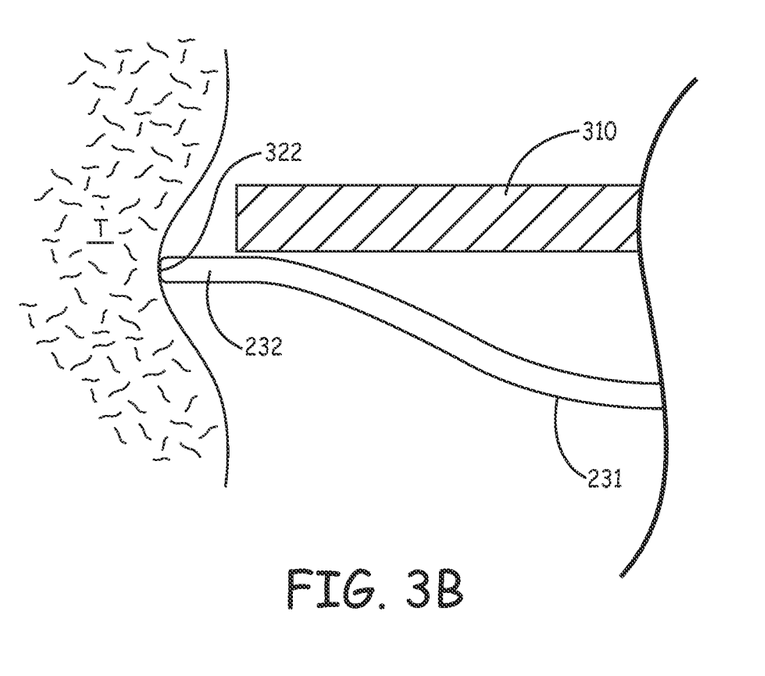
FIG. 3B is an enlarged detail view of one of the tine portions initially contacting tissue at an implant site.
Figure 3C:
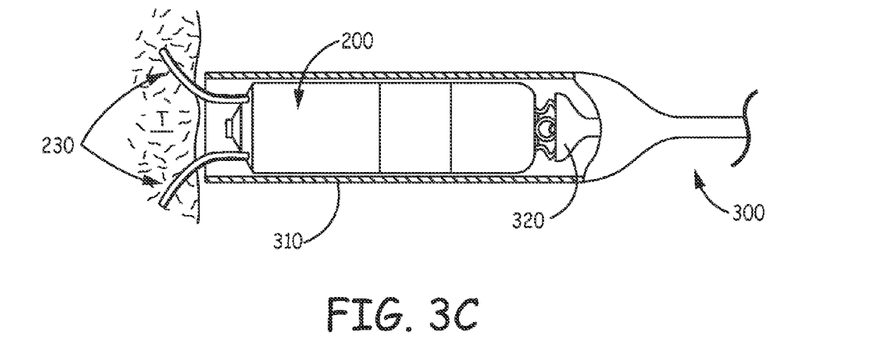
FIGS. 3C-D are plan views of the device and catheter in subsequent steps of implanting the device, when the tine portions have penetrated the tissue.
Figure 3D:
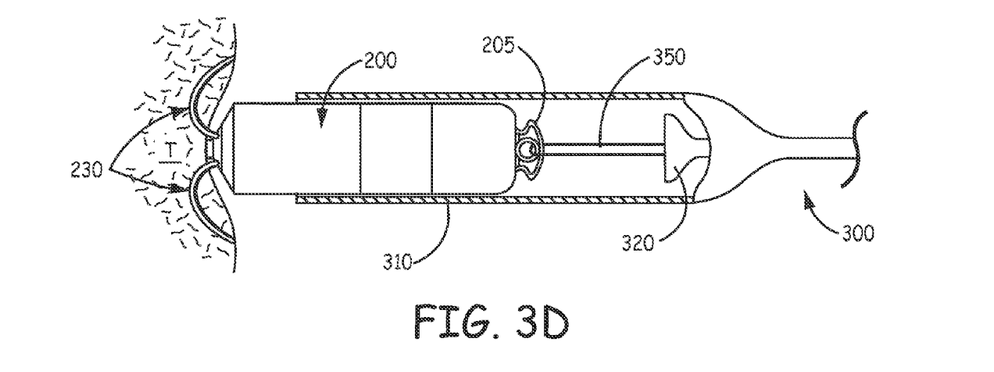

FIG. 3B, is an enlarged view of distal segment 232 of one of tine portions 230, wherein a tissue-piercing tip 322, which terminates distal segment 232, has just been pushed out through opening 313 of distal end 310 of catheter 300 and into contact with tissue T. FIG. 3B illustrates distal segment 232 supported by the surrounding wall of distal end 310, in proximity to opening 313, so that the push force of deployment element 320 is effectively transferred through tip 322 to first compress the tissue T, as shown, and then to pierce the tissue T for penetration therein, which is shown in FIGS. 3C-D. FIGS. 3C-D illustrate partial tine penetration and full tine penetration, respectively, as deployment element 320 continues to push device 200 out opening 313. It can be seen that the elastic nature of each tine portion 230, once the constraint of the distal end 310 is withdrawn, allows the corresponding hook segment 231 to relax back toward the pre-set curvature thereof within the tissue. The full penetration of tine portions 230, shown FIG. 3D, is representative of acute fixation of device 200 at the implant site, for example, for the evaluation of device performance (e.g., pacing and sensing via electrodes 261, 262). It should be noted that, at some implant sites, tine portions 230 may, at full penetration, extend back out from tissue T, for example, generally toward distal end 310 of catheter 300.

With further reference to FIG. 3D, a tether 350 is shown looping through an eye feature 205 formed at the proximal end of device 200; tether 350 extends proximally through a lumen of deployment element 320 to a proximal end 351 thereof, outside a proximal end of deployment element 320, which may be seen in FIG. 3A. Thus, if the performance of acutely fixated device 200 is unsatisfactory, the operator may use tether 350 to pull device 200 back into distal end 310, thereby withdrawing tine portions 230 from the tissue, so that device may be moved by delivery catheter 300 to another potential implant site. Alternately, if the acutely fixated device 200 performs satisfactorily, proximal end 351 of tether 350 may be severed to pull tether 350 out from eye feature 205 of device 200, and the fully penetrated tine portions 230 continue to fixate device 200 for chronic implant.

The aforementioned co-pending and commonly assigned U.S. patent application Ser. No. '690 discloses suitable embodiments of a fixation component having tine portions similar to tine portions 230, wherein the tine portions exhibit a suitable baseline performance, for example, in terms of a deployment force, an acute retraction force (for repositioning), atraumatic retraction, and acute and chronic fixation forces. Yet, there is still a need for new configurations of tine portions for implantable devices, like device 200, that may further enhance fixation.

SUMMARY

Embodiments of the present invention encompass implantable medical devices (e.g., cardiac pacemakers) and tissue-penetrating fixation components and subassemblies thereof, which include one or more tine portions configured for increased strain relief during the flexing thereof, either at initial implant (particularly in cases where the retraction of penetrated tines is necessary for repositioning the device), or when subject to cyclic loading during a chronic implant of the fixated device, for example, within a beating heart.

According to some preferred embodiments, a tine portion of a tissue-penetrating component of an implantable medical device includes a hook segment and a distal segment, wherein the hook segment has a round cross-section, and the distal segment has a flattened cross-section. The hook segment is pre-set to extend along a curvature that encloses an angle of between 135 degrees and 270 degrees, from a proximal end thereof to a distal end thereof, and which is elastically deformable from the pre-set curvature to an open position; and the distal segment is pre-set to extend along a relatively straight line, approximately tangent to the distal end of the hook segment. In some embodiments of tissue-penetrating components, one or a pair of tine portions are integrally formed, with a base portion, from a superelastic wire (e.g., Nitinol). A fixation subassembly for an implantable medical device, according to some embodiments, includes insulative members, between which the base portion(s) of one or a pair of the tissue-penetrating components is/are captured.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 4A:
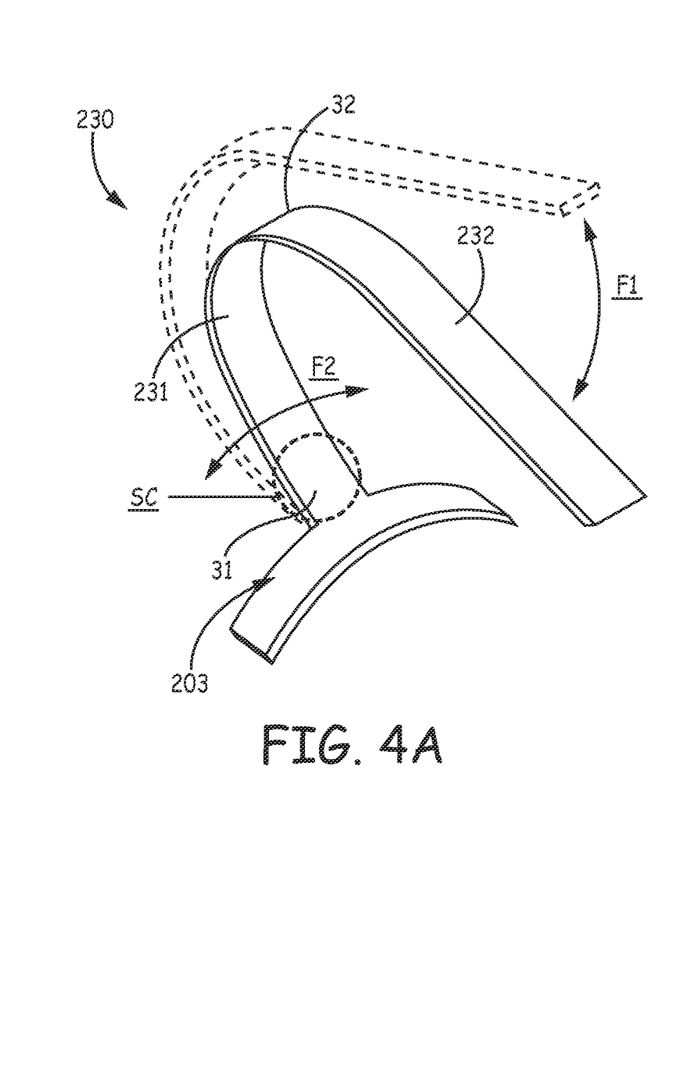
FIG. 4A is a schematic representation of a flexing tine portion.

FIG. 4A is a schematic representation of one of tine portions 230 isolated from the above-described implantable medical device 200, wherein exemplary flexing, per arrows F1, F2, of tine portion 230 is illustrated. Such flexing may be encountered by tine portion 230, once tine portion 230 has penetrated tissue to fix device 200 at a chronic implant site for cardiac monitoring and/or therapy, for example, as illustrated in FIG. 3D. Thus, fatigue life is a consideration influencing the configuration of tine portions for those implantable medical devices that may be subjected to cyclic loading caused by hundreds of millions of heart beats, over the life of their implant. In FIG. 4A, a zone of stress concentration SC, for example, in response to the flexing per arrows F1, F2, is circled; zone SC is located in proximity to a proximal end 31 of hook segment 231 of tine portion 230, where hook segment 231 joins with a base portion 203. Base portion 203 and tine portion 230 may be integrally formed, wherein base portion 203 is configured to be fixedly attached to device 200. Stress concentration in zone SC may also result from deformation of hook segment 231 into the open position (FIG. 3A), for example, upon initial loading of device 200 and retraction of device 200 back into distal end 310 of catheter for repositioning, which, in combination with the repeated force of deployment, can potentially push tine portion 230 toward an elastic limit and may make tine portion 230 subsequently more vulnerable to fatigue under the aforementioned cyclic loading. Although rounded edges of tine portions 230 effectively reduce the concentration of stress, as previously described in the aforementioned commonly-assigned U.S. patent application Ser. No. '690, embodiments of the present invention incorporate tine portions in which the hook segments thereof have round cross-sections, for example, as illustrated in FIG. 4B, as an alternative means of alleviating the stress concentration.

Figure 4B:
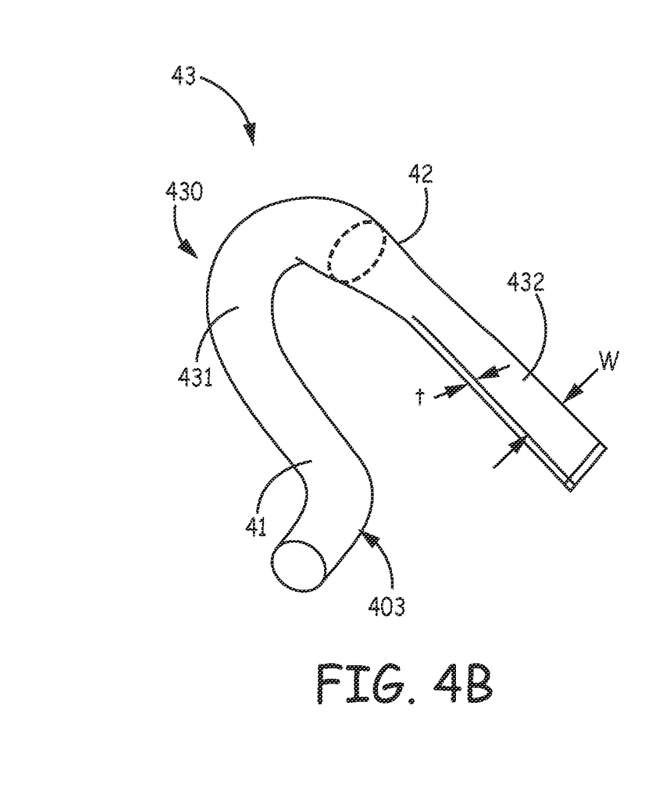
FIG. 4B is a perspective view of a tissue-penetrating fixation component, according to some embodiments of the present invention.

FIG. 4B is a perspective view of a tissue-penetrating fixation component 43, which includes a tine portion 430, according to some embodiments, one or more of which may be integrated into an implantable medical device 500, which is described below in conjunction with FIGS. 5A-B. A base portion 403 is shown integrally formed with tine portion 430, according to some preferred embodiments, wherein base portion 403 is configured for attachment to device 500. FIG. 4B illustrates a hook segment 431 of tine portion 430 extending from a proximal end 41 thereof, in proximity to base portion 403, to a distal end 42 thereof, in proximity to a distal segment 432 of tine portion 430, wherein hook segment 431 has a round cross-section (dashed line). FIG. 4B further illustrates distal segment 432 having a flattened cross-section, or an approximately rectangular profile, for example, similar to that of distal segment 232, wherein the edges spanning a thickness t thereof are rounded. According to an exemplary embodiment, the round cross-section of hook segment 432 has a diameter of approximately 0.007 inch to approximately 0.012 inch, thickness t of distal segment 432 is approximately 0.005 inch, and a width W of distal segment 432 is approximately 0.025 inch. It should be noted that, according to some alternate embodiments, hook segment 432 may have an elliptical cross-section, for example, having a major axis of approximately 0.012 inch and a minor axis of approximately 0.007 inch. Tine portion 430 and base portion 403 of component 43, according to some preferred embodiments, are integrally formed from a superelastic wire, for example, a medical grade Nitinol wire, wherein a wire forming process and a rolling or swaging process may be employed to manufacture component 43.

Figure 5A:
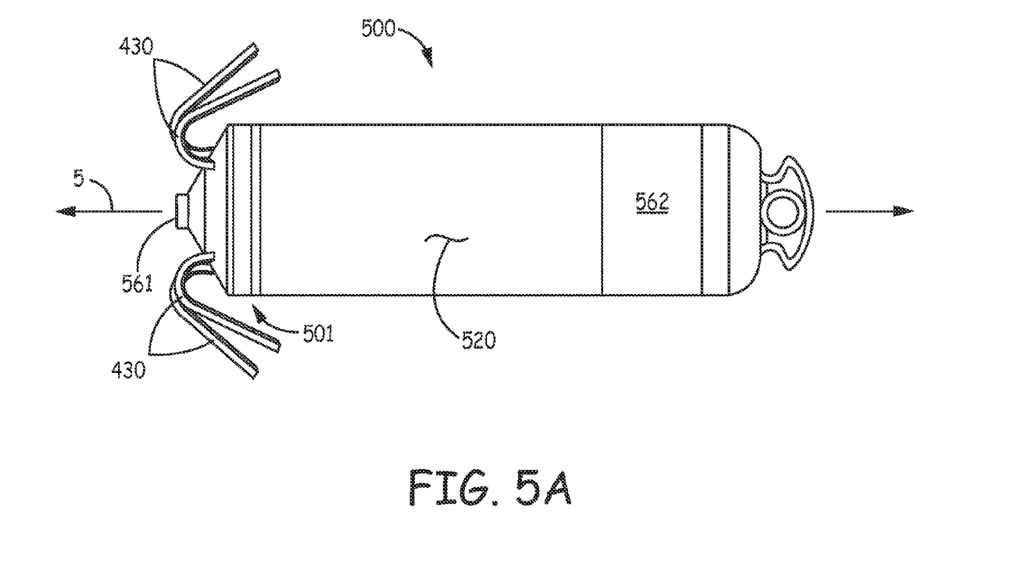
FIG. 5A is a plan view of an implantable medical device, according to some embodiments.
Figure 5B:
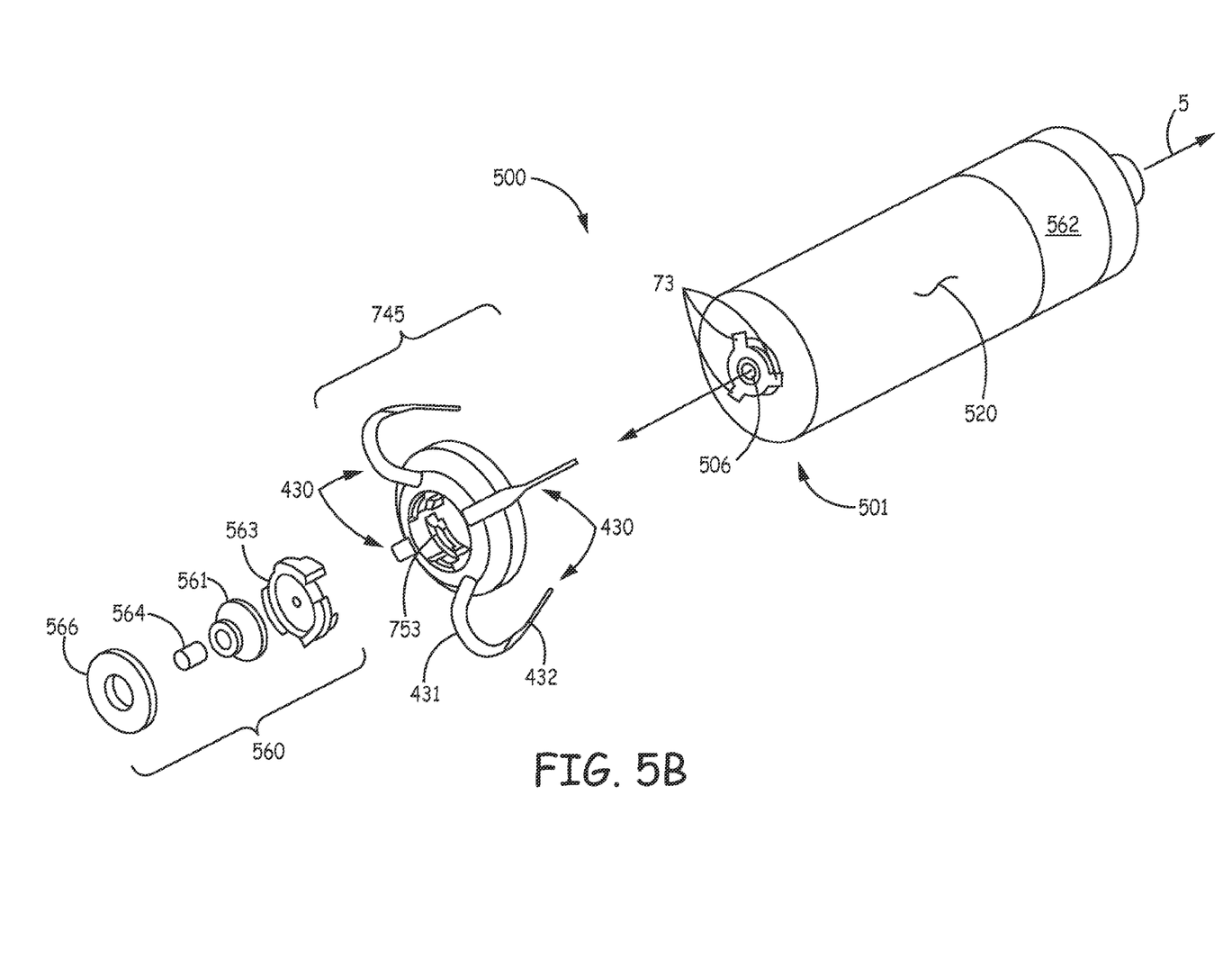
FIG. 5B is an exploded perspective view of the implantable medical device, according to some embodiments.

FIG. 5A is a plan view of implantable medical device 500; and FIG. 5B is an exploded perspective view of device 500, according to some embodiments. FIGS. 5A-B illustrates device 500 including a hermetically sealed housing 520 and a pair of electrodes 561, 562; housing 520 defines a longitudinal axis 5 of device 500, and contains control electronics and a power source (not shown), which, for example, together with electrodes 561, 562, are adapted for cardiac pacing and sensing. FIG. 5B further illustrates tine portions 430 included in fixation subassembly 745, which is configured for attachment to housing 520, via tabs 73 formed in a distal end 501 thereof, and illustrates electrode 561 included in an electrode subassembly 560, which is configured to fit together with fixation subassembly 745, according to some embodiments. Tine portions 430, like tine portions 230 described above, penetrate tissue in order to secure device 500 at an implant site, for example, a cardiac site in the right atrium RA or the right ventricle RV (FIG. 1), having been deployed from distal end 310 of delivery catheter 300 (FIGS. 3A-D).

With further reference to FIG. 5B, electrode subassembly 560 also includes steroid contained in a monolithic controlled release device (MCRD) 564, such as is known to those skilled in the art, which is configured to fit within a central recess of electrode 561; electrode 561 and MCRD 564 are sandwiched together between a cap 566 and an interlock interface component 563 of subassembly 560, when with electrode subassembly 560 and fixation subassembly 745 are assembled together at distal end 501 of housing 520. An hermetic feedthrough subassembly (not shown) for electrode 561, the construction of which is known to those skilled in the art, may extend into housing at the location designated with reference numeral 506. The aforementioned commonly-assigned U.S. patent application Ser. No. '690 describes in greater detail an exemplary means by which electrode 561 may be integrated into device 500, as well as additional construction details for an implantable medical device like device 500.

Figure 6A:
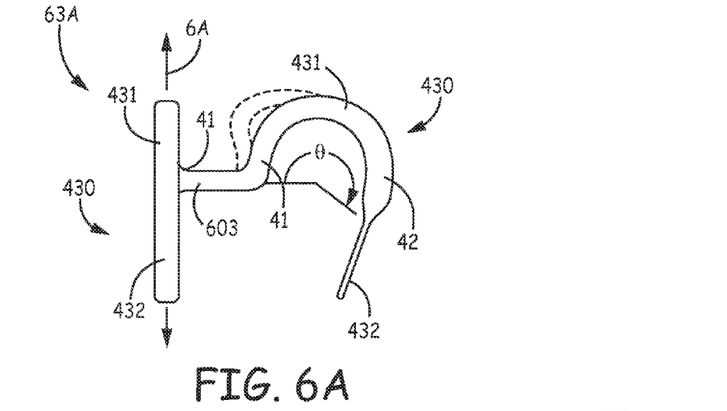
FIGS. 6A-C are elevation views of tissue-penetrating fixation components, according to some alternate embodiments.
Figure 6B:
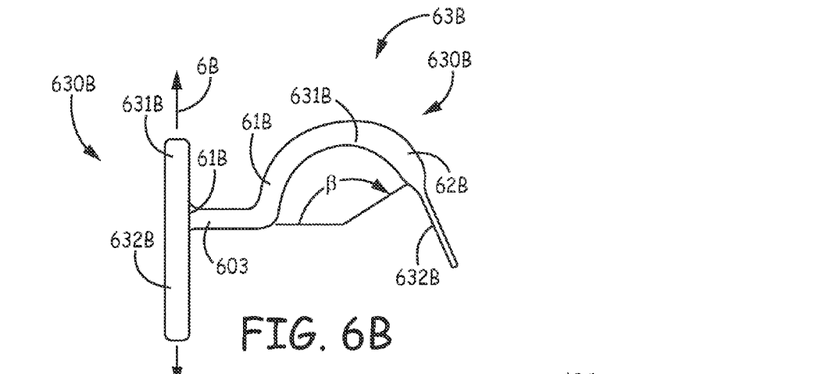
Figure 6C:
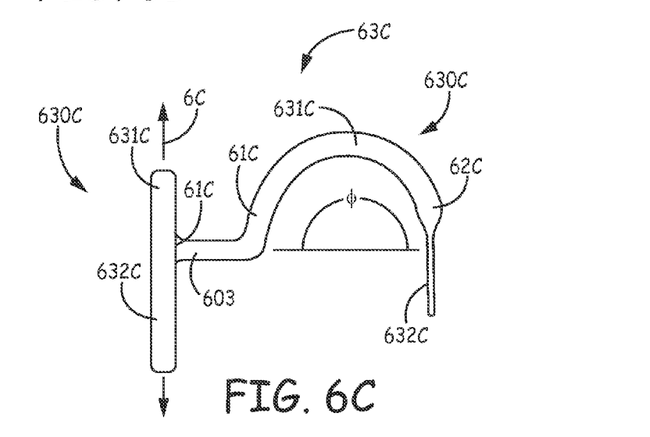

According to some preferred embodiments, adjacent pairs of tine portions 430 may be integrally formed together, for example, in a tissue penetrating component 63A, which is shown in FIG. 6A. FIGS. 6A-C are elevation views of various tissue-penetrating fixation components 63A-C, according to some alternate embodiments of the present invention. FIG. 6A illustrates component 63A including a base portion 603 that extends between proximal ends 41 of hook segments 431 of tine portions 430. According to the illustrated embodiment, base portion 603 extends along an arc (best seen in FIGS. 7A-B) that is centered on a longitudinal axis 6A of component 63A, wherein axis 6A approximately coincides with longitudinal axis 5 of device 500, when component 63A is included in subassembly 745. Likewise, FIGS. 6B-C illustrate each tissue-penetrating component 63B-C including a pair of tine portions 630A-B and corresponding base portion 603, which extends along an arc that is centered on a corresponding longitudinal axis

6B-C of the corresponding component 63B-C. As described above, tine portions 430, 630B-C and base portion 603 of each component 63A-C are preferably integrally formed from a superelastic wire, for example, Nitinol wire, wherein base portion 603 and hook segments 431, 631B-C have a round profile, while distal segments 432, 632B-C have a flattened profile. Alternately, the wire, from which tine portions 430, 630B-C are formed, may have an elliptical cross-section so that base portion 603 and hook segments 431, 631B-C likewise have an elliptical cross-section. Any suitable wire forming process known to those skilled in the art, for example, in the manufacture of spring component, may be employed to form components 63A-C, wherein a rolling swaging process may be employed to form the flattened cross-section of distal segments 432, 632B-C. Furthermore, according to some methods, a secondary stamping or cutting process may be employed to further form distal segments 432, 632B-C.

With reference to FIGS. 6A-C, components 63A-C differ from one another according to the pre-set curvatures of corresponding hook segments 431, 631B, 631C, as follows. According to FIG. 6A, each hook segment 431 is pre-set to extend along a curvature that encloses an angle $\Theta$ of between 180 degrees and 270 degrees, from proximal end 41 to distal end 42, such that the corresponding distal segment 432 extends from distal end 42, along a relatively straight line (approximately tangent to distal end 42) toward longitudinal axis 6A. According to FIG. 6B, each hook segment 631B is pre-set to extend along a curvature that encloses an angle $\beta$ of between 135 degrees and 180 degrees, preferably approximately 160 degrees, from proximal end 61B to distal end 62B, such that the corresponding distal segment 632B, extends from distal end 62B, along a relatively straight line (approximately tangent to distal end 62B) away from longitudinal axis 6B. According to FIG. 6C, each hook segment 631C is pre-set to extend along a curvature that encloses an angle $\phi$ of 180 degrees, from proximal end 61C to distal end 62C, such that the corresponding distal segment 632C, extends from distal end 62C, along a relatively straight line (approximately tangent to distal end 62C) that is approximately parallel to longitudinal axis 6B.

With further reference to FIGS. 6A-C, it may be noted that distal segments 632B, 632C of respective tine portions 630B, 630C are relatively short compared to distal segment 432 of each tine portion 430, for example, being between approximately 0.05 inch and approximately 0.1 inch. The shorter length of distal segments 632B-C may help to prevent perforation through the wall of a structure, for example, the heart, at some implant locations, when tine portions 630B-C, having been deformed into the open position for loading into a delivery catheter, for example, catheter 300 (FIG. 3A), are initially pushed into a target implant site (FIG. 3B-D). The shorter length may also help reduce a probability for penetrated tine portions 630B-C to interfere with blood vessels, for example, compressing or pinching the vessels. Furthermore, the pre-set curvature (defined by the aforementioned angles $\beta$, $\phi$) of hook segments 631B-C, in combination with the shorter length of distal segments 632B-C, can help to maintain an effective orientation of distal segments 632B-C for tissue penetration, when the corresponding hook segments 631B-C are deformed into the open position within distal end 310 of delivery catheter 300 in a manner similar to that illustrated in FIG. 3A.

With further reference to FIG. 6A, dashed lines illustrate an alternate configuration of hook segment 431, in proximity to proximal end 41 thereof. According to the alternate configuration, an extension of segment 431 from proximal end 41 toward axis 6A increases an overall arc length of tine portion 430 for added flexibility in elastically deforming hook segment 431 to the open position, for example, during retraction into catheter distal end 310 (FIGS. 3A-C). Although not shown, each hook segment 631B, 61C of the corresponding tine portion 630B, 630C (FIGS. 6B-C) may also be configured to extend from the corresponding proximal end 61B, 61C back toward the corresponding axis 6B, 6C, according to some alternate embodiments.

Figures 7A, 7B:
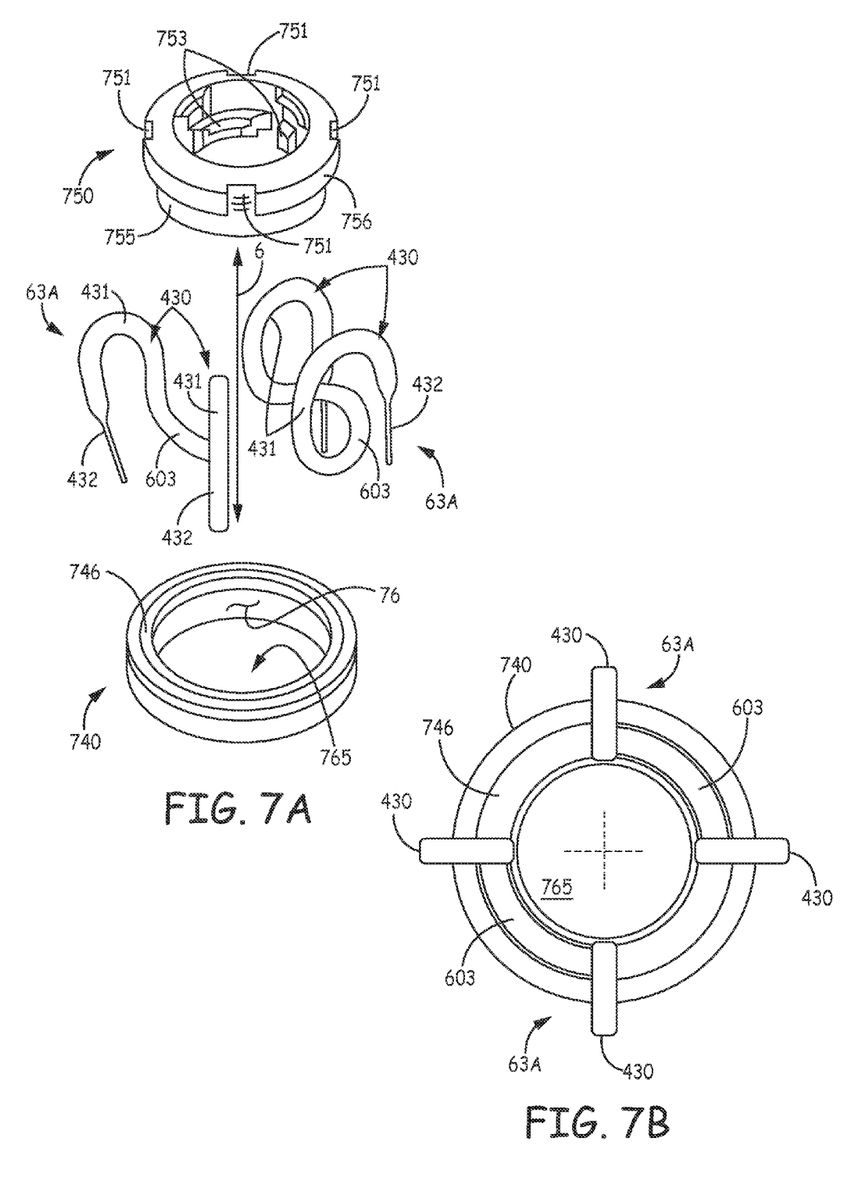
FIG. 7A is an exploded perspective view of a fixation subassembly, according to some embodiments.
FIG. 7B is a top plan view of portions of the fixation subassembly partially assembled.

FIG. 7A is an exploded perspective view of fixation subassembly 745, according to some embodiments; and FIG. 7B is a top plan view of portions of fixation subassembly 745 partially assembled. FIG. 7A illustrates fixation subassembly 745 including an insulative locking member 750, an insulative retainer 740, and a pair of the tissue-penetrating fixation components 63A, which may be exchanged for a pair of either of the components 63B, 63C, according to some alternate embodiments. FIG. 7A further illustrates locking member 750 including a collar 756 and a body 755 extending therefrom, wherein collar 756 includes a plurality of notches 751, which are formed in an outer perimeter surface thereof, and are spaced apart from one another about the perimeter. Retainer 740 is shown including a groove 746 formed therein, to receive base portions 603 of components 63A, and an internal surface 76, which defines an opening 765 to receive body 755 of locking member 750. According to an exemplary embodiment, retainer 740 and locking member 750 are formed, for example, by injection molding, from a relatively hard biocompatible plastic, such as polyether ether ketone (PEEK). FIG. 7B illustrates base portions 603 of fixation components 63A seated in groove 746 of retainer 740, such that tine portions 430 are spaced apart from one another, about the perimeter of retainer 740, by approximately 90 degrees. With further reference to FIG. 7A, notches 751 are similarly spaced about a perimeter of locking member 750, so that, when components 63A are seated in groove 746 of retainer 740, and body 755 of locking member 750 is received in opening 765 of retainer 740, each hook segment 431 extends through a corresponding notch 751. It should be noted that, according to some alternate embodiments, wherein three pair of tine potions 430 are employed, the spacing thereof, along with corresponding notches 751, about the perimeter of retainer 740, is approximately 60 degrees.

With reference back to FIG. 5B, in conjunction with FIG. 7A, according to some embodiments, locking member 750 further includes an internal surface with interlocking features 753 formed therein. According to the illustrated embodiment, features 753 are configured to mate with tabs 73, for example, by inserting each tab 73 through a slot adjacent each feature 753 and then rotating subassembly 745 to engage a ramped surface of each feature 753 beneath a corresponding tab 73. With further reference to FIG. 5B, interlock interface component 563 of electrode subassembly 560, may, when assembled together with fixation subassembly 745, engage within the slots to retain features 753 in engagement with tabs 73.

In the foregoing detailed description, the invention has been described with reference to specific embodiments. However, it may be appreciated that various modifications and changes can be made without departing from the scope of the invention as set forth in the appended claims.

The invention claimed is:

1. A tissue-penetrating fixation component for an implantable medical device comprising a base portion and at least one tine portion, the base portion being configured to be fixedly attached to the medical device, each of the at least one tine portion comprising a hook segment and a distal segment terminated by a tissue-piercing tip, the hook segment being pre-set to extend along a curvature that encloses an angle of between 135 degrees and 270 degrees, from a proximal end thereof, in proximity to the base portion, to a distal end thereof, the distal segment being pre-set to extend along a straight line, tangent to the distal end of the hook segment, from the distal end of the hook segment to the tip, and the hook segment being elastically deformable from the pre-set curvature to an open position; and wherein:

the hook segment of each tine portion has a round cross-section defined by a diameter and the distal segment of each tine portion has a flattened, or approximately rectangular cross-section.

2. The component of claim 1, wherein the angled enclosed by the pre-set curvature of the hook segment is greater than 180 degrees.

3. The component of claim 1, wherein the angle enclosed by the pre-set curvature of the hook segment is 180 degrees.

4. The component of claim 1, wherein the angle enclosed by the pre-set curvature of the hook segment is less than 180 degrees.

5. The component of claim 1, wherein the at least one tine portion and the base portion are integrally formed from a superelastic wire.

6. The component of claim 1, wherein:

the at least one tine portion comprises a first tine portion and a second tine portion;

the first and second tine portions and the base portion are integrally formed from a superelastic wire; and the base portion extends between the proximal ends of the hook segments.

7. The component of claim 6, wherein the base portion extends along an arc.

8. An implantable medical device comprising a hermetically sealed housing and a tissue-penetrating fixation member, the housing defining a longitudinal axis of the device, and the fixation member comprising at least one tine portion, each of the at least one tine portion comprising a hook segment and a distal segment terminated by a tissue-piercing tip, the hook segment being pre-set to extend along a curvature that encloses an angle of between 135 degrees and 270 degrees, from a proximal end thereof to a distal end thereof, the proximal end of the hook segment being located in proximity to the housing, the distal segment being pre-set to extend along a straight line, tangent to the distal end of the hook segment, from the distal end of the hook segment to the tip, and the hook segment being elastically deformable from the pre-set curvature to an open position; and wherein:

the hook segment of the at least one tine portion has a round cross-section defined by a diameter; and the distal segment of the at least one tine portion has a flattened, or approximately rectangular cross-section.

9. The device of claim 8, wherein the distal segment of each tine portion of the fixation member extends toward the longitudinal axis, when the hook segment of the tine portion conforms to the pre-set curvature.

10. The device of claim 8, wherein the distal segment of each tine portion of the fixation member extends parallel with the longitudinal axis, when the hook segment of the tine portion conforms to the pre-set curvature.

11. The device of claim 8, wherein the distal segment of each tine portion of the fixation member extends away from the longitudinal axis, when the hook segment of the tine portion conforms to the pre-set curvature.

12. The device of claim 8, wherein:
the at least one tine portion of the fixation member comprises a first tine portion and a second tine portion;
the fixation member further comprises a base portion;
the tine portions and the base portion of the fixation member are integrally formed from a superelastic wire; and
the base portion extends between the proximal ends of the hook segments.

13. The device of claim 8, wherein the base portion of the fixation member extends along an arc.

14. A tissue-penetrating fixation component for an implantable medical device comprising:
a superelastic wire including first, second and third portions, the wire having a round or elliptical cross-section along the first portion, and a flattened cross-section along the second and third portions, the first portion of the wire forming a base and two tine hook segments, and the second and third portions of the wire forming two tine distal segments, each tine distal segment being terminated by a tissue-piercing tip; and
wherein each of the two tine hook segments is pre-set to extend along a curvature that encloses an angle of between 135 degrees and 270 degrees, from a proximal end thereof to a distal end thereof, each tine hook segment being elastically deformable from the pre-set curvature to an open position;
each of the two tine distal segments extends from the distal end of a corresponding tine hook segment, each tine distal segment being pre-set to extend along a straight line, tangent to the distal end of the corresponding tine hook segment, from the distal end of the corresponding tine hook segment to the corresponding tip; and
the base is configured to be fixedly attached to the medical device and extends between the proximal ends of the two tine hook segments.

15. The component of claim 14, wherein the base of the first portion of the wire extends along an arc.

16. The component of claim 14, wherein the angle enclosed by the pre-set curvature of each of the two tine hook segments is greater than 180 degrees.

17. The component of claim 14, wherein the angle enclosed by the pre-set curvature of each of the two tine hook segments is 180 degrees.

18. The component of claim 14, wherein the angle enclosed by the pre-set curvature of each of the two tine hook segments is less than 180 degrees.

* * * * *

UNITED STATES PATENT AND TRADEMARK OFFICE
CERTIFICATE OF CORRECTION

PATENT NO.       : 9,579,500 B2  
APPLICATION NO.  : 14/831417  
DATED            : February 28, 2017  
INVENTOR(S)      : Kenneth D. Rys et al.

Page 1 of 1

It is certified that error appears in the above-identified patent and that said Letters Patent is hereby corrected as shown below:

On the Title Page

Item (71) delete "Minneapolis, MA" and insert in place thereof --Minneapolis, Minnesota--

In the Claims

Claim 2 Line 17 delete "the angled enclosed..." and insert in place thereof --the angle enclosed...--

Signed and Sealed this  
Nineteenth Day of December, 2017

Joseph Matal  
*Performing the Functions and Duties of the*  
*Under Secretary of Commerce for Intellectual Property and*  
*Director of the United States Patent and Trademark Office*